(12) United States Patent
Silverberg et al.

(10) Patent No.: US 12,304,895 B2
(45) Date of Patent: May 20, 2025

(54) 2,3-DIARYL-2,3-DIHYDRO-4H-1,3-THIAZIN-4-ONE COMPOUNDS AND METHODS FOR MAKING

(71) Applicant: The Penn State Research Foundation, University Park, PA (US)

(72) Inventors: Lee J. Silverberg, Allentown, PA (US); John Tierney, West Chester, PA (US)

(73) Assignee: THE PENN STATE RESEARCH FOUNDATION UNIVERSITY, University Park, PA (US)

( * ) Notice: Subject to any disclaimer, the term of this patent is extended or adjusted under 35 U.S.C. 154(b) by 768 days.

(21) Appl. No.: 17/609,916

(22) PCT Filed: May 21, 2020

(86) PCT No.: PCT/US2020/034021
§ 371 (c)(1),
(2) Date: Nov. 9, 2021

(87) PCT Pub. No.: WO2020/237063
PCT Pub. Date: Nov. 26, 2020

(65) Prior Publication Data
US 2022/0213046 A1    Jul. 7, 2022

Related U.S. Application Data

(60) Provisional application No. 62/852,093, filed on May 23, 2019.

(51) Int. Cl.
C07D 279/06    (2006.01)
C07D 279/08    (2006.01)
C07D 513/04    (2006.01)

(52) U.S. Cl.
CPC ......... C07D 279/06 (2013.01); C07D 279/08 (2013.01); C07D 513/04 (2013.01)

(58) Field of Classification Search
CPC ............... C07D 279/06; C07D 279/08; C07D 513/04; A61P 31/04; A61P 35/00
(Continued)

(56) References Cited

U.S. PATENT DOCUMENTS 3,082,209 A    3/1963    Surrey et al.

FOREIGN PATENT DOCUMENTS

| CN | 102653526 A | 9/2012 |
| CN | 102786493 A | 11/2021 |
| WO | 2008/112674 A1 | 9/2008 |

OTHER PUBLICATIONS

Aljamali ,Synthesis and characterization of new cycles of selenazane and thiazane, Pharma Innovation (2013), 1(11), 73-79) (Year: 2013).*

(Continued)

Primary Examiner — Taylor V Oh
(74) Attorney, Agent, or Firm — Buchanan Ingersoll & Rooney PC

(57) ABSTRACT

A compound with the following general formula (I) and a general method of making this compound are provided. $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ are each independently selected from the group that includes H, halogen, nitro, cyano, amido, pyridyl, alkyl, aryl, acyl, alkoxy, cycloalkyl, heteroalkyl, heterocyclyl, aralkyl, heteroaryl and heteroaralkyl.

(Continued)

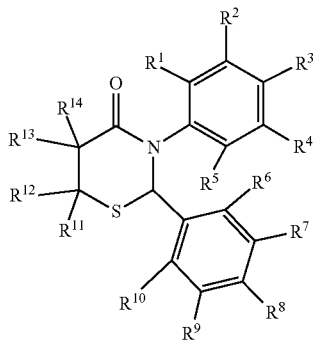

(I)

9 Claims, 3 Drawing Sheets

(58) Field of Classification Search
USPC .......................................................... 544/48
See application file for complete search history.

(56) References Cited

OTHER PUBLICATIONS

Yennawar et al., Crystal structures of 2-(4-nitrophenyl)-3-phenyl-2,3-dihydro-4H-1,3-benzothiazin-4-one and 2-(2-nitrophenyl)-3-phenyl-2,3-dihydro-4H-1,3-benzothiazin-4-one, Acta Cryst. (2015). E71, 414-417 (Year: 2015).*

Yennawar et al., Crystal structures of three substituted 3-aryl-2-phenyl-2,3-dihydro-4H-1,3-benzothiazin-4-ones, Acta Cryst. (2016)E72, 1108-1112, ear: 2016) (Year: 2016).* .

Yennawar et al.,Spontaneous resolution and crystal structure of (2S)-2-(3-nitro phen yl)-3-phenyl-2,3,5,6-tetra hydro-4H-1,3-thia zin-4-one; crystal structure of rac-2-(4-nitro phen yl)-3-phenyl-2,3,5,6-tetra hydro-4H-1,3t Acta Crystallographica, Section E: Crystallographic Communications (2018), 74(4), 454-457.*

Written Opinion of the International Searching Authority for PCT/US2020/034021, dated Sep. 10, 2020.

International Search Report for PCT/US2020/034021, dated Sep. 10, 2020.

Silverberg et al., Synthesis and Spectroscopic Properties of 2,3-Diphenyl-1,3-thiaza-4-one Heterocycles, International Journal of Chemistry, 2015, pp. 150-162, vol. 7, No. 2, Canada.

PubChem CID 44517771, 2009, 2, PubChem, available: https://pubchem.ncbi.nlm.nih.gov/compound/44517771.

PubChem CID 22090046, 2007, 2, PubChem, available: https://pubchem.ncbi.nlm.nih.gov/compound/22090046.

PubChem CID 139088178, 2019, PubChem, available: https://pubchem.ncbi.nlm.nih.gov/compound/139088178.

PubChem CID 10490981, 2006, 2, PubChem, available: https://pubchem.ncbi.nlm.nih.gov/compound/10490981.

PubChem CID 139086145, 2019, 2, PubChem, available: https://pubchem.ncbi.nlm.nih.gov/compound/139086145.

Lee J. Silverberg et al., Synthesis and Spectroscopic Properties of a Series of Novel 2-Aryl-3-Phenyl-2,3-Dihydro-4H-1,3-Benzothiazin-4-Ones, Arkivoc, 2016, pp. 122-143, vol. 2016, No. 6.

Mogilaiah K. et al, Synthesis and Antimicrobial Activity of 1,8-Naphthyridinyl-4-Thiazolidinones/1,3-Thiazin-4-Ones/2-Azetidinones, Indian Journal of Chemistry, Section B, 1999, pp. 495-500, vol. 38B, No. 4.

Nagham Mahmood Aljamali, Synthesis and Characterization of New Cycles of Selenazane and Thizane, The Pharma Innovation, 2013, pp. 73-79, vol. 1, No. 11.

Hemant P. Yennawar et al., Crystal Structure of N-[(2S, 5R)-4-oxo-2,3-diphenyl-1,3-thiazinan-5-yl]acetamide 0.375-hydrate, Acta Crsytallographica Section E, 2015, pp. 62-64, vol. 71(Pt 1).

* cited by examiner

2,3-DIARYL-2,3-DIHYDRO-4H-1,3-THIAZIN-4-ONE COMPOUNDS AND METHODS FOR MAKING

CROSS-REFERENCE TO RELATED APPLICATIONS

This application claims the benefit of U.S. Provisional Patent Application No. 62/852,093, filed on May 23, 2019, which is incorporated by reference in its entirety.

BACKGROUND OF THE INVENTION

Field of the Invention

The present invention relates to a six-membered 1,3-thiazin-4-one ring system.

Compounds with an N-aryl-2,3,5,6-tetrahydro-4H-1,3-thiazin-4-one scaffold (Formula 1) have been shown to have a variety of bioactivities, including antifungal,[1-3] antitubercular,[2] antitumor,[4] antidiabetic,[5] regulation of plant growth,[3] cleavage of DNA (possible antitumor),[6] inhibition of cannabinoid receptor 1 (CB1),[7] and inhibition of angiogenesis (possible treatment of eye disease, neoplasm, arteriosclerosis, arthritis, psoriasis, diabetes, and mellitus).[8]

Compounds with a 2,3-dihydro-4H-1,3-benzothiazin-4-one scaffold (FIG. 2) have shown a wide range of bioactivity, including antimalarial,[9] antitumor,[10-12] antimicrobial,[13] and HIV-RT inhibitory.[14-15] N-aryl ($R^1$=aryl or heteroaryl) compounds in this family have also shown antitumor,[10,12,16] antimicrobial,[17] HIV-RT inhibitory activity,[14] as well as cyclooxygenase COX-2 enzyme inhibition.[18] Of the 46 privileged scaffolds identified by Welsch, Snyder, and Stockwell in 2010,[19] a remarkable 23 contained a benzene ring fused to a heterocycle, although this heterocycle was not on that list.

Compounds with a 2,3-dihydro-4H-pyrido[3,2-e][1,3]thiazin-4-one scaffold (FIG. 3) have shown anticancer,[20] antibacterial,[21] and glycosidase inhibitory[22] bioactivity.

SUMMARY OF THE INVENTION

The present invention is directed to 2,3-diaryl-2,3-dihydro-4H-1,3-thiazin-4-ones.

One aspect of the present invention is directed to a compound of Formula I.

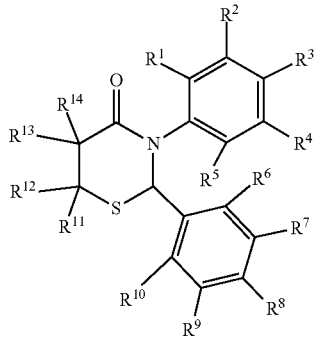

I $R^1, R^2, R^3, R^4, R^5, R^6, R^7, R^8, R^9, R^{10}, R^{11}, R^{12}, R^{13}$ and $R^{14}$ are each independently selected from the group that includes H, halogen, nitro, cyano, amido, pyridyl, alkyl, aryl, acyl, alkoxy, cycloalkyl, heteroalkyl, heterocyclyl, aralkyl, heteroaryl and heteroaralkyl. In some embodiments $R^3$ and $R^8$ are not H or $CH_3$. $R^3$ may also not be an aza-aromatic group. In other embodiments, $R^3$ is a thiazinone.

Another aspect of the present invention is directed to a compound with the following structure:

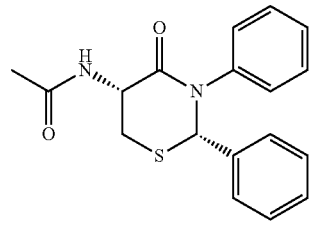 [SMILES: CC(=O)N[C@H]1CS[C@@H](c2ccccc2)N(c2ccccc2)C1=O]

Another aspect of the present invention is directed to a compound of Formula II:

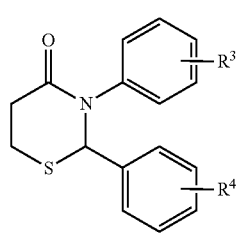

II

In one embodiment, $R^3$ is H; and $R^4$ is selected from the group that includes H, m-$NO_2$, p-$NO_2$, m-Br, p-Br, m-F, p-F, m-$CF_3$, p-$CF_3$, m-$CH_3$, p-$CH_3$, m-$OCH_3$ and p-$OCH_3$.

In another embodiment, $R^3$ is selected from the group that includes m-$NO_2$, p-Br, m-F, p-F, m-$CF_3$, p-$CH_3$ and m-$OCH_3$; and $R^4$ is H. In other embodiments, $R^3$ is a p-thiazinone. Preferably, in other embodiments $R^3$ is a p-benzothiazinone.

Another aspect of the present invention is directed to a compound of Formula III:

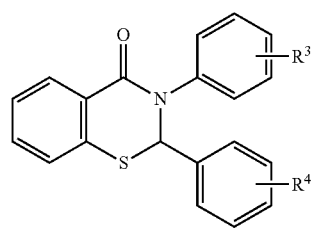

III

In one embodiment, $R^3$ is H; and $R^4$ is selected from the group that includes H, o-$NO_2$, m-$NO_2$, p-$NO_2$, m-Br, p-Br, m-F, p-F, m-$CF_3$, p-$CF_3$, m-$CH_3$, p-$CH_3$, m-$OCH_3$ and p-$OCH_3$.

In another embodiment, $R^3$ is selected from the group that includes m-$NO_2$, m-Br, p-Br, m-F, p-F, m-$CF_3$, p-$CF_3$, m-$CH_3$, p-$CH_3$, m-$OCH_3$ and p-$OCH_3$; and $R^4$ is H. In other embodiments $R^3$ is a p-benzothiazinone.

In another embodiment, $R^3$ and $R^4$ are each selected from the group that includes m-Br, p-Br, m-F, p-F, m-$CF_3$, p-$CF_3$, m-$CH_3$, p-$CH_3$, m-$OCH_3$ and p-$OCH_3$; and $R^3$ is the same as $R^4$.

Another aspect of the present invention is directed to a compound of Formula IV:

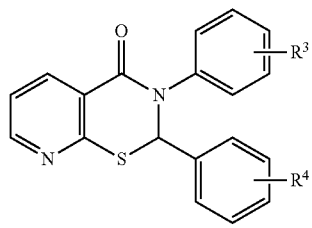

In one embodiment, $R^3$ is H; and $R^4$ is selected from the group that includes H, m-$NO_2$, p-$NO_2$, m-Br, p-Br, p-F, m-$CF_3$, p-$CF_3$, m-$CH_3$, m-$OCH_3$ and p-$OCH_3$.

Other aspects and advantages of the invention will be apparent from the following description and the appended claims.

DETAILED DESCRIPTION OF THE INVENTION

Definitions

Figure 1:
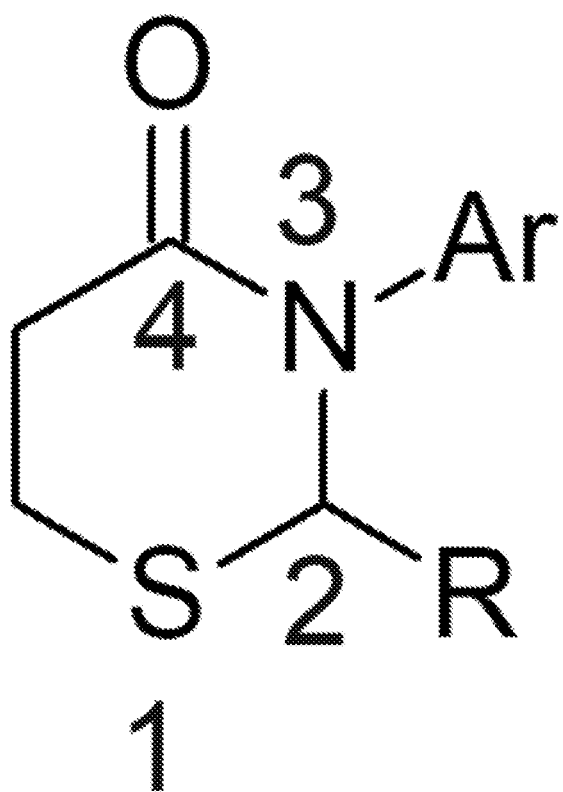
FIG. 1. 2,3,5,6-Tetrahydro-4H-1,3-thiazin-4-ones skeleton.
Figure 2:
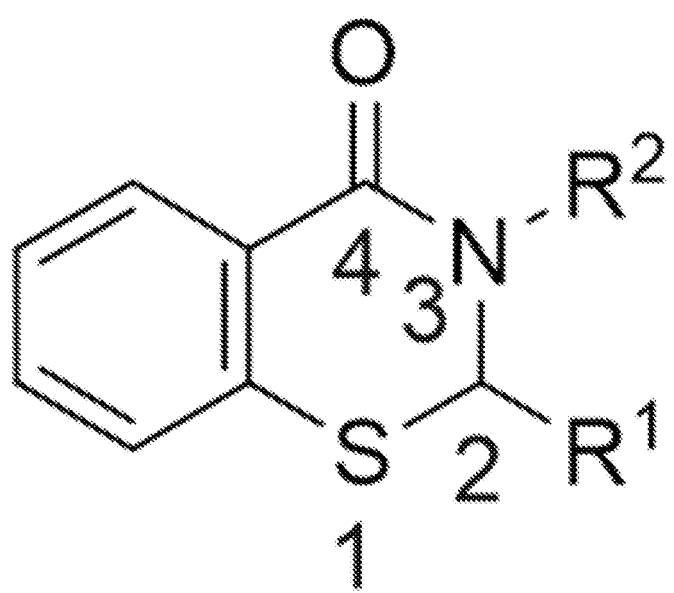
FIG. 2. 2,3-Dihydro-4H-1,3-benzothiazin-4-one skeleton.
Figure 3:
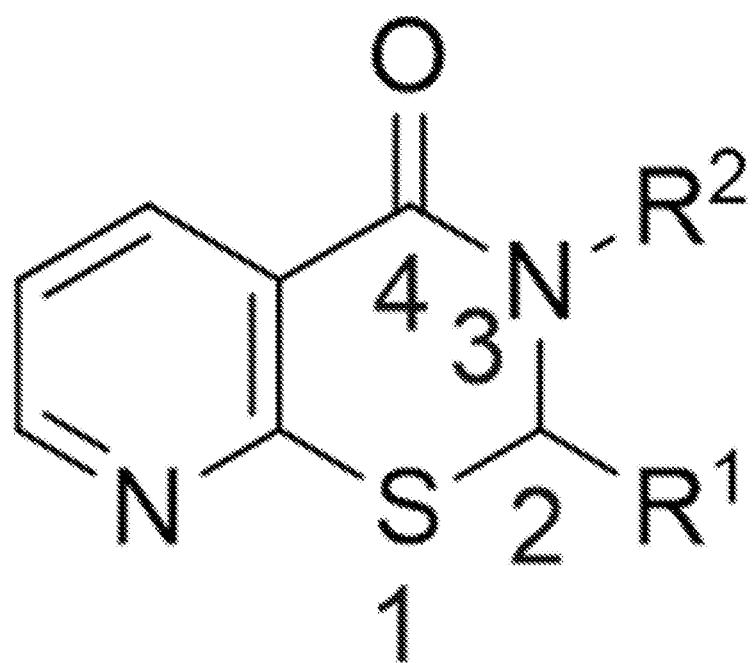
FIG. 3. 2,3-Dihydro-4H-pyrido[3,2-e][1,3]thiazin-4-one skeleton.

While the terms used herein are believed to be well understood by one of ordinary skill in the art, definitions are set forth herein to facilitate explanation of the subject matter disclosed herein.

Unless defined otherwise, all technical and scientific terms used herein have the same meaning as commonly understood by one of ordinary skill in the art to which the subject matter disclosed herein belongs. Although any methods, devices, and materials similar or equivalent to those described herein can be used in the practice or testing of the presently disclosed subject matter, representative methods, devices, and materials are described herein.

The terms "a," "an," and "the" refer to "one or more" when used in this application, including the claims. The use of the word "a" or "an" when used in conjunction with the term "comprising" in the claims and/or the specification may mean "one," but it is also consistent with the meaning of "one or more," "at least one," and "one or more than one."

The term "alkyl" includes branched, straight chain and cyclic, substituted or unsubstituted saturated aliphatic hydrocarbon groups. Alkyl groups can comprise about 1 to about 24 carbon atoms ("C1-C24"), about 7 to about 24 carbon atoms ("C7-C24"), about 8 to about 24 carbon atoms ("C8-C24"), or about 9 to about 24 carbon atoms ("C9-C24"). Alkyl groups can also comprise about 1 to about 8 carbon atoms ("C1-C8"), about 1 to about 6 carbon atoms ("C1-C6"), or about 1 to about 3 carbon atoms ("C1-C3"). Examples of C1-C6 alkyl groups include, but are not limited to, methyl, ethyl, propyl, isopropyl, butyl, sec-butyl, tert-butyl, pentyl, isopentyl, neopentyl, hexyl, isohexyl, cyclohexyl, cyclohexylmethyl, cyclopropylmethyl and neohexyl radicals.

The term "aryl" includes a 6- to 14-membered monocyclic, bicyclic or tricyclic aromatic hydrocarbon ring system. Examples of an aryl group include phenyl and naphthyl.

The term "heteroaryl" includes an aromatic heterocycle ring of 5 to 14 members and having at least one heteroatom selected from nitrogen, oxygen and sulfur, and containing at least 1 carbon atom, including monocyclic, bicyclic, and tricyclic ring systems. Representative heteroaryls are triazolyl, tetrazolyl, oxadiazolyl, pyridyl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, quinazolinyl, pyrimidyl, oxetanyl, azepinyl, piperazinyl, morpholinyl, dioxanyl, thietanyl and oxazolyl.

All references to singular characteristics or limitations of the present disclosure shall include the corresponding plural characteristic(s) or limitation(s) and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The methods and devices of the present disclosure, including components thereof, can comprise, consist of, or consist essentially of the essential elements and limitations of the embodiments described herein, as well as any additional or optional components or limitations described herein or otherwise useful.

Unless otherwise indicated, all numbers expressing physical dimensions, quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently disclosed subject matter.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The following description is of exemplary embodiments that are presently contemplated for carrying out the present invention. This description is not to be taken in a limiting sense, but is made merely for the purpose of describing the general principles and features of the present invention. The scope of the present invention is not limited by this description.

Experimental

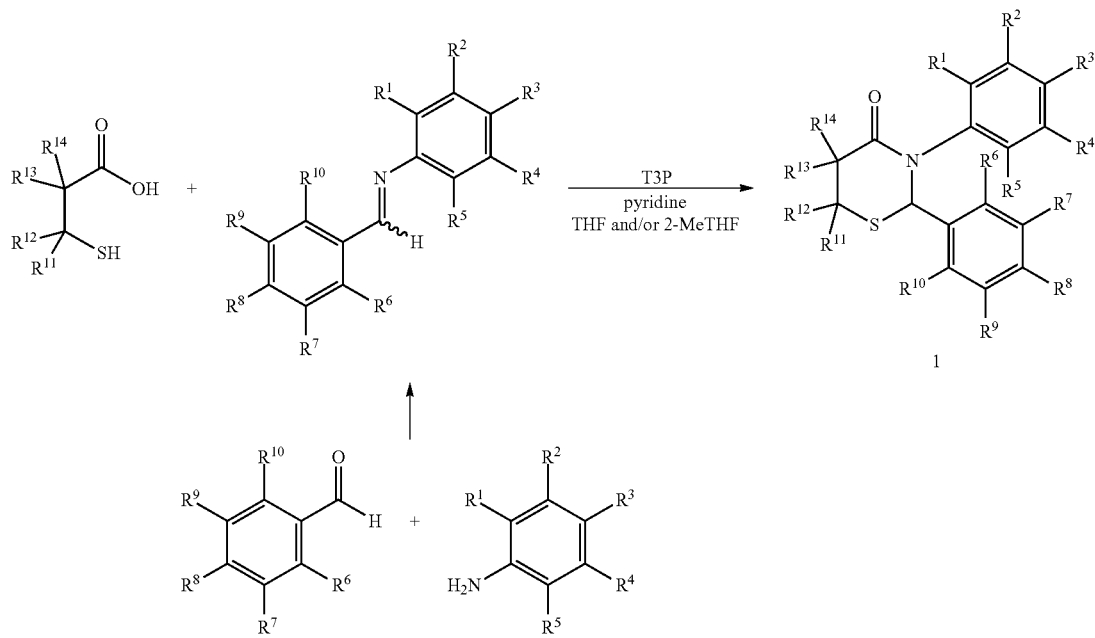

General Procedure for the Preparation of 2,3-Diaryl-2,3-dihydro-4H-1,3-thiazin-4-ones A two-necked 25-mL roundbottom flask was oven-dried, cooled under $N_2$, and charged with a stir bar and an imine (6 mmol), or alternatively the precursor aldehyde and amine (6 mmol each). Tetrahydrofuran or 2-methyltetrahydrofuran (2.3 mL) was added and the solution was stirred. Pyridine (1.95 mL, 24 mmol or 2.9 mL, 36 mmol) was added and then a 3-thio-1-carboxylic acid [HS—C—C—C(O)OH] (6 mmol) was added. Finally, 2,4,6-tripropyl-1,3,5,2,4,6-trioxatriphosphorinane-2,4,6-trioxide (T3P) in 2-methyltetrahydrofuran (50 weight percent; 7.3 mL, 12 mmol or 11 mL, 18 mmol) was added. The reaction was stirred at room temperature and followed by TLC, then poured into a separatory funnel with dichloromethane (20 mL). The mixture was washed with water (10 mL). The aqueous was then extracted twice with dichloromethane (10 mL each). The organics were combined and washed with saturated sodium bicarbonate (10 mL) and then saturated sodium chloride (10 mL). The organic was dried over sodium sulfate and concentrated under vacuum to give a crude mixture. Further purification was carried out as indicated below for each compound.

2,3-diphenyl-2,3-dihydro-4H-1,3-benzothiazin-4-one: After chromatography on 30 g silica gel with mixtures of ethyl acetate and hexanes, slow recrystallization from ethanol gave slightly yellow crystals (0.6676 g, 35% yield). mp: 136-137° C. $^1$H NMR (CDCl$_3$): δ(ppm): 8.24 (d, 1H, J=7.3 Hz), 7.45-7.18 (m, 13H), 6.07 (s, 1H).

2,3-Diphenyl-2,3,5,6-tetrahydro-4H-1,3-thiazin-4-one: After chromatography on 30 g silica gel with mixtures of ethyl acetate and hexanes, recrystallization from propanol gave slightly yellow solid (1.1379 g, 70% yield). mp: 94-96° C. $^1$H NMR (CDCl$_3$): δ (ppm): 7.42-7.21 (m, 10H), 5.91 (s, 1H), 3.06-2.87 (m, 4H).

2,3-diphenyl-2,3-dihydro-4H-pyrido[3,2-e][1,3]thiazin-4-one: After chromatography on 30 g silica gel with mixtures of ethyl acetate and hexanes, recrystallization from ethanol gave white solid (0.6927 g, 36% yield). mp: 134-135° C. $^1$H NMR (CDCl$_3$): δ (ppm): 8.50 (dd, 1H, J=4.8, 1.8 Hz), 8.46 (dd, 1H, J=7.7, 1.8 Hz), 7.7 (d, 2H, J=7.7 Hz), 7.41 (m, 2H), 7.35 (m, 2H), 7.32-7.26 (m, 4H), 7.21 (m, 1H), 6.17 (s, 1H).

N-[(2S,5R)-4-oxo-2,3-diphenyl-1,3-thiazinan-5-yl]acetamide: The crude product was shown to possess 61:39 diastereomeric ratio and after chromatography, fractions containing mainly the major product were combined then recrystallized from toluene to give 0.1575 g. Mixed fractions that contained the major product were combined and recrystallized from acetone, yielding the major product in two crops, 0.4189 g and 0.1839 g (total of the three crops 0.7603 g, 41% yield). The three crops were combined (0.681 g) and recrystallized again from acetone (0.381 g, 55.9% recovery, 23% overall yield). White powder. mp: 190-192° C. $^1$H NMR (CDCl$_3$): δ (ppm): 7.32-7.17 (m, 8H), 7.05 (m, 2H), 6.82 (br. s, 1H, J=5.1 Hz), 6.09 (s, 1H), 4.99-4.95 (dt, 1H, J=11.4, 5.8 Hz), 3.62-3.58 (dd, 1H, J=12.1, 6.3 Hz), 2.95 (t, 1H, J=11.9 Hz), 2.10 (s, 3H).

2-(2-Nitrophenyl)-3-phenyl-2,3-dihydro-4H-1,3-benzothiazin-4-one: After chromatography on 30 g silica gel with mixtures of ethyl acetate and hexanes, recrystallization from ethanol yielded 0.301 g (14% yield). mp: 172-177° C. $^1$H NMR (CDCl$_3$): δ(ppm): 8.25 (d, 1H, J=7.3 Hz), 8.10 (d, 1H, J=8.5 Hz), 7.63 (m, 2H), 7.52 (t, 1H, J=7.3 Hz), 7.47-7.41 (m, 3H), 7.36-7.32 (m, 3H), 7.29 (t, 1H, J=7.3 Hz), 7.11 (d, 1H, J=8.5 Hz), 7.01 (s, 1H).

2-(4-Nitrophenyl)-3-phenyl-2,3-dihydro-4H-1,3-benzothiazin-4-one: After chromatography on 30 g silica gel with mixtures of ethyl acetate and hexanes, recrystallization from gave ethanol gave off-white crystals (0.67 g, 30% yield). mp: 180-183° C. $^1$H NMR (CDCl$_3$): δ(ppm): 8.23 (dd, 1H, J=7.9, 1.3 Hz), 8.14 (d, 2H, J=8.8 Hz), 7.63 (d, 2H, J=8.8 Hz), 7.42 (m, 2H), 7.38 (td, 1H, J=7.6, 1.7 Hz), 7.33 (d, 3H, J=7.7 Hz), 7.31 (m, 1H), 7.19 (dd, 1H, J=7.7, J=0.7 Hz), 6.12 (s, 1H).

2-(3-Nitrophenyl)-3-phenyl-2,3-dihydro-4H-1,3-benzothiazin-4-one: After chromatography on 30 g silica gel with mixtures of ethyl acetate and hexanes, recrystallization from ethyl acetate/hexanes gave light yellow crystals (0.8659 g, 40% yield). mp: 163-165° C. $^1$H NMR (CDCl$_3$): δ(ppm): 8.36 (s, 1H), 8.24 (d, 1H, J=9.8 Hz), 8.12 (d, 1H, J=6.1 Hz), 7.79 (d, 1H, J=7.3 Hz), 7.49-7.29 (m. 8H), 7.20 (d, 1H, J=7.3 Hz), 6.14 (s, 1H).

3-Phenyl-2-[4-(trifluoromethyl)phenyl]-2,3-dihydro-4H-1,3-benzothiazin-4-one (1d). After chromatography on 30 g silica gel with mixtures of ethyl acetate and hexanes, recrystallization from isopropanol/water gave fine white crystals (0.87 g, 38% yield). mp: 137-139° C. $^1$H NMR (CDCl$_3$): δ(ppm): 8.24 (d, 1H, J=7.3 Hz), 7.57 (t, 4H, J=8.5 Hz), 7.43-7.29 (m, 7H), 7.19 (d, 1H, J=8.5 Hz), 6.08 (s, 1H).

3-Phenyl-2-[3-(trifluoromethyl)phenyl]-2,3-dihydro-4H-1,3-benzothiazin-4-one: The imine was used as a crude liquid. After chromatography on 30 g silica gel with mixtures of ethyl acetate and hexanes, the material was triturated with hexanes to give a pale yellow solid (0.4959 g). Recrystallization from cyclohexane gave white flakes (0.28 g, 12% yield). mp: 114-115° C. $^1$H NMR (CDCl$_3$): δ(ppm): 8.23 (d, 1H, J=7.6 Hz), 7.71 (s, 1H), 7.63 (d, 1H, J=7.3 Hz), 7.51 (d, 1H, J=7.3 Hz), 7.41-7.29 (m 8H), 7.20 (d, 1H, J=7.6 Hz), 6.10 (s 1H).

2-(4-Bromophenyl)-3-phenyl-2,3-dihydro-4H-1,3-benzothiazin-4-one: After chromatography on 30 g silica gel with mixtures of ethyl acetate and hexanes, recrystallization from isopropanol gave fine off-white crystals (0.83 g, 35% yield). mp: 148-151° C. $^1$H NMR (CDCl$_3$): δ(ppm): 8.22 (d, 1H, J=7.3 Hz), 7.40 (t, 4H, J=7.9 Hz), 7.37-7.27 (m, 7H), 7.19 (d, 1H, J=8.5 Hz), 6.01 (s, 1H).

2-(3-Bromophenyl)-3-phenyl-2,3-dihydro-4H-1,3-benzothiazin-4-one: After chromatography on 30 g silica gel with mixtures of ethyl acetate and hexanes, recrystallization from methanol gave tan crystals (0.54 g, 23% yield). mp: 118-120° C. $^1$H NMR (CDCl$_3$): δ(ppm): 8.23 (d, 1H, J=9.8 Hz), 7.60 (s. 1H), 7.42-7.28 (m, 9H), 7.20 (d, 1H, J=7.3 Hz), 7.15 (m, 1H), 6.01 (s, 1H).

2-(4-Fluorophenyl)-3-phenyl-2,3-dihydro-4H-1,3-benzothiazin-4-one: After chromatography on 30 g silica gel with mixtures of ethyl acetate and hexanes, recrystallization from ethanol/water gave white crystals (0.30 g, 15% yield). mp: 100-105° C. $^1$H NMR (CDCl$_3$): δ(ppm): 8.23 (d, 1H, J=8.1 Hz), 7.43-7.27 (m, 9H), 7.20 (d, 1H, J=7.7 Hz), 6.96 (t, 2H, J 8.3 Hz), 6.06 (s, 1H).

2-(3-Fluorophenyl)-3-phenyl-2,3-dihydro-4H-1,3-benzothiazin-4-one: After chromatography on 30 g silica gel with mixtures of ethyl acetate and hexanes, recrystallization from dichloromethane/hexanes gave off-white powder (0.86 g, 43% yield). mp: 102-103° C. $^1$H NMR (CDCl$_3$): δ(ppm): 8.23 (dd, 1H, J=7.8, 1.1 Hz), 7.42-7.16 (m, 11H), 6.95 (apparent t with fine splitting, 1H), 6.04 (s, 1H).

2-(4-Methylphenyl)-3-phenyl-2,3-dihydro-4H-1,3-benzothiazin-4-one: Hot filtration in ethanol followed by recrystallization from toluene/hexanes gave yellowish crystals (0.57 g, 30% yield). mp: 108-111° C. $^1$H NMR (CDCl$_3$): δ(ppm): 8.24 (d, 1H, J=8.1 Hz), 7.39-7.25 (m, 10H), 7.18 (d, 1H, J=7.7 Hz), 7.08 (d, 1H, J=7.7 Hz), 6.03 (s, 1H), 2.30 (s, 3H).

2-(3-Methylphenyl)-3-phenyl-2,3-dihydro-4H-1,3-benzothiazin-4-one (11). The imine was used as a crude liquid. After chromatography on 30 g silica gel with mixtures of ethyl acetate and hexanes, recrystallization from acetonitrile/water gave colorless crystals (0.31 g, 16% yield from crude imine). mp: 91-95° C. $^1$H NMR (CDCl$_3$): δ(ppm): 8.24 (d, 1H, J=8.5 Hz), 7.40-7.34 (m, 5H), 7.30-7.26 (m, 2H), 7.23 (s, 2H), 7.18 (m, 2H), 7.06 (d, 1H, J=7.3 Hz), 6.02 (s, 1H), 2.30 (s, 3H).

2-(4-Methoxyphenyl)-3-phenyl-2,3-dihydro-4H-1,3-benzothiazin-4-one: After chromatography on 30 g silica gel with mixtures of ethyl acetate and hexanes, recrystallization from ethanol gave fine white solid (0.70 g). Recrystallization of the solid from dichloromethane/hexanes produced shiny white crystals (0.67 g, 32% yield). mp: 136.5-139.5° C. $^1$H NMR (CDCl$_3$): δ(ppm): 8.23 (dd, 1H, J=8.1, 1.1 Hz), 7.39-7.34 (m, 7H), 7.29-7.26 (m, 2H), 7.19 (m, 1H), 6.80 (m, 2H), 6.04 (s, 1H), 3.76 (s, 3H).

2-(3-Methoxyphenyl)-3-phenyl-2,3-dihydro-4H-1,3-benzothiazin-4-one: The imine was used as a crude liquid. After chromatography on 30 g silica gel with mixtures of ethyl acetate and hexanes, recrystallization from ethanol gave fine white crystals (0.84 g, 40% yield from crude imine). mp: 125-127° C. $^1$H NMR (CDCl$_3$): δ(ppm): 8.23 (dd, 1H, J=7.9, 1.3 Hz), 7.40-7.34 (m, 5H), 7.30-7.26 (m, 2H), 7.19 (m, 2H), 7.01 (m, 1H), 6.97 (m, 1H), 6.79 (dd, 1H, J=8.3, 2.4 Hz), 6.02 (s, 1H), 3.74 (s, 3H).

3-(3-nitrophenyl)-2-phenyl-2,3-dihydro-4H-1,3-benzothiazin-4-one: After chromatography on 30 g silica gel with mixtures of ethyl acetate and hexanes, recrystallization from 2-propanol produced pale yellow solid (0.7415 g, slightly impure by TLC and NMR). A second crop gave 0.027 g, total 0.7685 g. Recrystallization of 0.6914 g of the combined solids from dichloromethane/methanol gave pale yellow solid (0.5025 g, 72.7% recovery, overall 26% yield). mp: 168-170° C. A second crop of 0.0708 g was isolated (total yield 0.5733 g, 29%). $^1$H NMR (CDCl$_3$): δ(ppm): 8.23 (m, 2H), 8.14 (d, 1H, J=8.5 Hz), 7.68 (d, 1H, J=7.3 Hz), 7.55 (m, 1H), 7.43 (d, 2H, J=7.3 Hz), 7.39 (d, 1H, J=7.3 Hz), 7.39-7.28 (m, 4H), 7.22 (d, 1H, J=7.3 Hz), 6.14 (s, 1H).

2-phenyl-3-[4-(trifluoromethyl)phenyl]-2,3-dihydro-4H-1,3-benzothiazin-4-one: After chromatography on 30 g silica gel with mixtures of ethyl acetate and hexanes, recrystallization from dichloromethane/hexanes gave yellow solid (0.5639 g, 24% yield). mp: 131-133° C. $^1$H NMR (CDCl$_3$): δ(ppm): 8.23 (d, 1H, J=8.5 Hz), 7.64 (dq, 2H, J=8.5, 0.7 Hz), 7.48 (dq, 2H, J=8.5, 0.7 Hz), 7.43 (d, 2H, J=6.1 Hz), 7.37 ((m, 1H), 7.30 (m, 4H), 7.20 (d, 1H, J=8.5 Hz), 6.09 (s, 1H).

2-phenyl-3-[3-(trifluoromethyl)phenyl]-2,3-dihydro-4H-1,3-benzothiazin-4-one: After chromatography on 30 g silica gel with mixtures of ethyl acetate and hexanes, trituration with hexanes gave a solid. Recrystallization from ligroin (90-110° C. boiling range) gave off-white solid (0.5574 g, 24% yield). mp: 113-117° C. $^1$H NMR (CDCl$_3$): δ(ppm): 8.23 (d, 1H, J=7.3 Hz), 7.64 (s, 1H), 7.52 (m, 3H), 7.43 (d, 2H, J=6.7 Hz), 7.38 (t, 1H, J=7.3 Hz), 7.30 (d, 4H, J=7.0 Hz), 7.21 (d, 1H, J=7.3 Hz), 6.09 (s, 1H).

3-(4-bromophenyl)-2-phenyl-2,3-dihydro-4H-1,3-benzothiazin-4-one: After chromatography on 30 g silica gel with mixtures of ethyl acetate and hexanes, recrystallization from 2-propanol gave bright yellow powder (0.6802 g, 29% yield). mp: 116-118° C. $^1$H NMR (CDCl$_3$): δ(ppm): 8.22 (d, 1H, J=6.7 Hz), 7.49 (d, 2H, J=8.5 Hz), 7.40 (d, 2H, J=6.4 Hz), 7.35 (m, 1H), 7.28 (d, 4H, J=7.0 Hz), 7.22 (d, 2H, J=8.5 Hz), 7.19 (d, 1H, J=7.6 Hz), 6.02 (s, 1H).

3-(3-bromophenyl)-2-phenyl-2,3-dihydro-4H-1,3-benzothiazin-4-one: After chromatography on 30 g silica gel with mixtures of ethyl acetate and hexanes, trituration from hexanes gave solid. Recrystallization from toluene/hexanes gave white solid in two crops (total 0.6601 g, 28% yield). mp 1st crop: 123-125° C. $^1$H NMR (CDCl$_3$): δ(ppm): 8.22 (d, 1H, J=7.6 Hz), 7.55 (s, 1H), 7.42 (d, 3H, J=6.1 Hz), 7.36 (m, 1H), 7.27 (m, 7H), 7.19 (d, 2H, J=6.7 Hz), 6.05 (s, 1H).

3-(4-fluorophenyl)-2-phenyl-2,3-dihydro-4H-1,3-benzothiazin-4-one: Recrystallization from toluene gave white solid (0.8556 g, 43% yield). mp: 167-170° C. $^1$H NMR (CDCl$_3$): δ(ppm): 8.23 (d, 1H, J=7.7 Hz), 7.41 (dd, 2H, J=8.3 Hz), 7.36 (m, 1H), 7.32-7.26 (m, 6H), 7.19 (d, 1H, J=7.7 Hz), 7.06 (pseudo triplet, 2H, J=8.3 Hz), 6.01 (s, 1H).

3-(3-fluorophenyl)-2-phenyl-2,3-dihydro-4H-1,3-benzothiazin-4-one: After chromatography on 30 g silica gel with mixtures of ethyl acetate and hexanes, recrystallization from ethanol/water produced yellow solid (0.5291 g, 26% yield). mp: 88-91° C. $^1$H NMR (CDCl$_3$): δ(ppm): 8.23 (d, 1H, J=7.6 Hz), 7.42 (d, 2H, J=7.7 Hz), 7.37-7.26 (m. 7H), 7.20 (d, 1H, J=7.7 Hz), 7.12 (dtd, 2H, J=9.5, 2.2, 1.0 Hz), 7.00 (td, 1H, J=8.5, 1.0 Hz), 6.06 (s, 1H).

3-(4-methylphenyl)-2-phenyl-2,3-dihydro-4H-1,3-benzothiazin-4-one: After chromatography on 30 g silica gel with mixtures of ethyl acetate and hexanes, recrystallization from a mixture of 2-propanol and water gave a small amount of impure yellow solid (0.0494 g). Slow evaporation of the mother liquor then gave large, translucent, slightly yellow crystals (0.3453 g, 17% yield). mp: 95-106° C. $^1$H NMR (CDCl$_3$): δ(ppm): 8.23 (d, 1H, J=7.9 Hz), 7.43 (d, 2H, J=7.3 Hz), 7.37-7.17 (m, 8H), 7.18 (m, 2H), 6.03 (s, 1H), 2.36 (s, 3H).

3-(3-methylphenyl)-2-phenyl-2,3-dihydro-4H-1,3-benzothiazin-4-one: After chromatography on 30 g silica gel with mixtures of ethyl acetate and hexanes, recrystallization from 2-propanol gave off-white solid (0.8376 g, 42% yield). mp: 106-110° C. $^1$H NMR (CDCl$_3$): δ(ppm): 8.23 (d, 1H, J=7.9 Hz), 7.44 (d, 2H, J=7.3 Hz), 7.35-7.21 (m, 7H), 7.18 (d, 1H, J=7.9 Hz), 7.11 (t, 2H, J=6.7 Hz), 6.04 (s, 1H), 2.35 (s, 3H).

3-(4-methoxyphenyl)-2-phenyl-2,3-dihydro-4H-1,3-benzothiazin-4-one: After chromatography on 30 g silica gel with mixtures of ethyl acetate and hexanes, recrystallization from ethanol gave pale yellow solid (0.7222 g, 35% yield). mp: 92-96° C. $^1$H NMR (CDCl$_3$): δ(ppm): 8.22 (d, 1H, J=7.8 Hz), 7.41 (d, 2H, J=7.8 Hz), 7.33 (m, 1H), 7.28-7.23 (m, 7H), 7.17 (d, 1H, J=7.8 Hz), 6.89 (d, 2H, J=8.8 Hz), 5.99 (s. 1H), 3.81 (s, 3H).

3-(3-methoxyphenyl)-2-phenyl-2,3-dihydro-4H-1,3-benzothiazin-4-one: After chromatography on 30 g silica gel with mixtures of ethyl acetate and hexanes, 1.193 g of material that was solid at −10° C. but oil at room temperature was obtained. Recrystallization of 1.0902 g from ethyl acetate/hexanes gave white crystals (0.6192 g, 57% recovery, 36% yield). mp: 84-86° C. $^1$H NMR (CDCl$_3$): δ(ppm): 8.23 (dd, 1H, J=7.8, 1.3 Hz), 7.43 (d, 2H, J=7.4 Hz), 7.34 (td, 1H, J=7.6, 1.5 Hz), 7.31-7.20 (m, 6H), 7.18 (d, 1H, J=7.7 Hz), 6.96-6.87 (m 2H), 6.84 (dd, 1H, J=8.3, 2.4 Hz), 6.05 (s, 1H), 3.78 (s, 3H).

2,3-di(3-bromophenyl)2,3-dihydro-4H-1,3-benzothiazin-4-one: The crude solid was recrystallized twice from 2-propanol to give light yellow solid (0.5922 g, 21%). mp: 143-145° C. $^1$H NMR (CDCl$_3$): δ(ppm): 8.22 (d, 1H, J=7.9 Hz), 7.59 (s, 1H), 7.54 (s, 1H), 7.45, (d, 1H, J=7.6 Hz), 7.39 (m, 2H), 7.35-7.26 (m, 5H), 7.21 (d, 1H, J=7.9 Hz), 7.16 (m, 1H), 5.99 (s, 1H).

2,3-di(4-bromophenyl)2,3-dihydro-4H-1,3-benzothiazin-4-one: After chromatography on 30 g silica gel with mixtures of ethyl acetate and hexanes, recrystallization from toluene gave solid (0.4089 g, 14% yield). mp: 211° C. H NMR (CDCl$_3$): δ(ppm): 8.21 (d, 1H, J=7.9 Hz), 7.51 (m, 2H), 7.42 (d, 2H, J=8.2 Hz), 7.38 (m, 1H), 7.29 (m, 4H), 7.20 (m, 3H), 5.96 (s, 1H).

2,3-di(3-fluorophenyl)2,3-dihydro-4H-1,3-benzothiazin-4-one: Chromatography on 30 g silica gel with mixtures of ethyl acetate and hexanes gave an orange solid (1.23 g, 58% yield). mp: 53-55° C. $^1$H NMR (CDCl$_3$): δ(ppm): 8.22 (dd, J=7.9, 1.5 Hz, 1H), 7.42-7.32 (m, 2H), 7.32-7.23 (m, 3H), 7.21 (ddd, J=7.8, 3.0, 1.2 Hz, 2H), 7.18-7.08 (m, 3H), 7.06-6.92 (m, 2H), 6.03 (s, 1H).

2,3-di(3-(trifluoromethyl)phenyl)2,3-dihydro-4H-1,3-benzothiazin-4-one: Recrystallization from 2-propanol gave white solid (0.5199 g, 19% yield). mp: 119-120° C. $^1$H NMR (CDCl$_3$): δ(ppm): 8.23 (dd, 1H, J=7.8, 1.4 Hz), 7.71 (s, 1H), 7.64-7.61 (m, 2H), 7.58-7.48 (m, 4H), 7.44-7.39 (m, 2H), 7.32 (td, 1H, J=7.6, 1.2 Hz), 7.23 (dd, 1H, J=7.6, 0.9 Hz), 6.13 (s, 1H).

2,3-di(4-(trifluoromethyl)phenyl)2,3-dihydro-4H-1,3-benzothiazin-4-one: After chromatography on 30 g silica gel with mixtures of ethyl acetate and hexanes, recrystallization from acetone gave white solid (0.4895 g, 18% yield). mp: 217-220° C. $^1$H NMR (CDCl$_3$): δ(ppm): 8.24 (dd, 1H, J=7.9, 1.2 Hz), 7.67 (d, 2H, J=8.2 Hz), 7.57 (s, 4H), 7.47 (d, 2H, J=8.2 Hz), 7.42-7.38 (td, 1H, J=7.6, 1.5 Hz), 7.33-7.30 (td, 1H, J=7.6, 1.2 Hz), 7.21 (dd, 1H, J=7.9, 0.9 Hz), 6.10 (s, 1H)

2,3-di(3-methylphenyl)2,3-dihydro-4H-1,3-benzothiazin-4-one: Chromatography on 30 g silica gel with mixtures of ethyl acetate and hexanes gave orange solid (1.007 g, 49% yield). mp: 96-99° C. $^1$H NMR (CDCl$_3$): δ(ppm): 8.23 (d, 1H, J=7.6 Hz), 7.35-7.05 (m, 11H), 6.00 (s, 1H), 2.35 (s, 3H), 2.30 (s, 3H).

2,3-di(4-methylphenyl)2,3-dihydro-4H-1,3-benzothiazin-4-one: After chromatography on 30 g silica gel with mixtures of ethyl acetate and hexanes, recrystallization from 2-propanol gave white crystals (0.6288 g, 30% yield). mp: 139-141° C. $^1$H NMR (CDCl$_3$): δ(ppm): 8.23 (d, 1H, J=7.9 Hz), 7.35-7.32 (m, 1H), 7.30 (d, 2H, J=7.9 Hz), 7.28-7.24 (m, 1H), 7.17 (d, 3H, J=7.9 Hz), 7.08 (d, 2H, J=7.9 Hz), 5.99 (s, 1H), 2.36 (s, 3H), 2.29 (s, 3H).

2,3-di(3-methoxyphenyl)2,3-dihydro-4H-1,3-benzothiazin-4-one: After chromatography on 30 g silica gel with mixtures of ethyl acetate and hexane, the mixture was dissolved in hot methanol and filtered, concentrated, treated with activated carbon in CH$_2$Cl$_2$, concentrated and again dissolved in hot methanol and filtered. It was concentrated to yellow oil (0.6805 g, 30% yield). $^1$H NMR (CDCl$_3$): δ(ppm): 8.22 (d, 1H, J=7.7 Hz), 7.35 (t, 1H, J=7.5 Hz), 7.28 (d, 2H, J=7.3 Hz), 7.19 (m, 2H), 7.00 (dd, 1H, J=7.7, 0.7 Hz), 6.93 (m, 3H), 6.84 (d, 1H, J=8.2 Hz), 6.78 (d, 1H, J=7.9 Hz), 6.01 (s, 1H), 3.79 (s, 3H), 3.74 (s, 3H).

2,3-di(4-methoxyphenyl)2,3-dihydro-4H-1,3-benzothiazin-4-one: After chromatography on 30 g silica gel with mixtures of ethyl acetate and hexanes, recrystallization from ethanol gave light yellow solid (0.6379 g, 28% yield). mp: 118-120° C. $^1$H NMR (CDCl$_3$): δ(ppm): 8.22 (dd, 1H, J=7.9, 1.2 Hz), 7.36-7.23 (m, 7H), 7.18 (dd, 1H, J=7.8, 1.1 Hz), 6.90-6.87 (m, 2H), 6.80-6.77 (m, 2H), 5.97 (s, 1H), 3.81 (s, 3H), 3.76 (s, 3H).

2-(4-nitrophenyl)-3-phenyl-2,3,5,6-tetrahydro-4H-1,3-thiazin-4-one: After chromatography on 30 g silica gel with mixtures of ethyl acetate and hexanes, recrystallization from 2-propanol gave white powder (1.3970 g, 74% yield). mp: 137-139° C. $^1$H NMR (CDCl$_3$): δ(ppm): 8.25 (d, 2H, J=8.8 Hz), 7.60 (d, 2H, J=8.9 Hz), 7.35 (m, 2H), 7.25 (m, 1H), 7.19 (d, 2H, J=7.3 Hz), 6.00 (s, 1H), 3.00 (m, 4H).

2-(3-nitrophenyl)-3-phenyl-2,3,5,6-tetrahydro-4H-1,3-thiazin-4-one: After chromatography on 30 g silica gel with mixtures of ethyl acetate and hexanes, recrystallization from 2-propanol gave light yellow solid (1.1706 g, 62% yield). mp: 142° C. $^1$H NMR (CDCl$_3$): δ(ppm): 8.29 (t, 1H, J=2.0 Hz), 8.17 (ddd, 1H, J=8.1, 2.1, 0.8 Hz), 7.75 (dt, 1H, J=7.9, 0.8 Hz), 7.57 (t, 1H, J=7.9 Hz), 7.34 (m, 2H), 7.26-7.19 (m, 3H), 6.04 (s, 1H), 3.11-2.97 (m, 4H).

3-phenyl-2-(4-(trifluoromethy)phenyl)-2,3,5,6-tetrahydro-4H-1,3-thiazin-4-one: Chromatography on 30 g silica gel with mixtures of ethyl acetate and hexanes, gave pale yellow solid (1.3742 g, 68% yield). mp: 83-84° C. $^1$H NMR (CDCl$_3$): δ(ppm): 7.66 (d, 2H, J=7.0 Hz), 7.55 (d, 2H, J=7.0 Hz), (7.35-7.2 (m, 5H), 5.96 (s, 1H), 3.05-2.92 (m, 4H).

3-phenyl-2-(3-(trifluoromethyl)phenyl)-2,3,5,6-tetrahydro-4H-1,3-thiazin-4-one: Chromatography on 30 g silica gel with mixtures of ethyl acetate and hexanes gave yellow oil (1.3971 g, 69% yield). $^1$H NMR (CDCl$_3$): δ(ppm): 7.67 (s, 1H), 7.60 (m, 2H), 7.52 (m, 1H), 7.35-7.24 (m, 3H), 7.20 (d, 2H, J=8.5 Hz), 5.98 (s, 1H), 3.05-2.96 (m, 4H).

2-(4-bromophenyl)-3-phenyl-2,3,5,6-tetrahydro-4H-1,3-thiazin-4-one: After chromatography on 30 g silica gel with mixtures of ethyl acetate and hexanes, recrystallization from 2-propanol/water gave white crystals (0.9613 g, 46%). mp 79-81° C. $^1$H NMR (CDCl$_3$): δ(ppm): 7.51 (m, 2H, 7.35-7.18 (m, 7H), 5.87 (s, 1H), 3.02-2.92 (m, 4H).

2-(3-bromophenyl)-3-phenyl-2,3,5,6-tetrahydro-4H-1,3-thiazin-4-one: Chromatography on 30 g silica gel with mixtures of ethyl acetate and hexanes gave light yellow solid (1.1482 g, 55% yield). mp: 85-87° C. $^1$H NMR (CDCl$_3$): δ(ppm): 7.48 (s, 1H), 7.36 (d, 1H, J=7.7 Hz), 7.27-7.24 (m, 3H), 7.19-7.15 (m, 3H), 7.11 (d, 2H, J=8.4 Hz), 5.77 (s, 1H), 2.96-2.79 (m, 4H).

2-(4-fluorophenyl)-3-phenyl-2,3,5,6-tetrahydro-4H-1,3-thiazin-4-one: After chromatography on 30 g silica gel with mixtures of ethyl acetate and hexanes, recrystallization from CH$_2$Cl$_2$/hexanes gave colorless crystals (0.8653 g, 50% yield). mp: 102-103° C. $^1$H NMR (CDCl$_3$): δ(ppm): 7.38 (ddt, J=8.1, 4.6, 2.4 Hz, 2H), 7.35-7.30 (m, 2H), 7.24 (tt, J=6.8, 1.1 Hz, 1H), 7.21-7.15 (m, 2H), 7.11-7.03 (m, 2H), 5.92 (s, 1H), 3.16-2.78 (m, 4H).

2-(3-fluorophenyl)-3-phenyl-2,3,5,6-tetrahydro-4H-1,3-thiazin-4-one: After chromatography on 30 g silica gel with mixtures of ethyl acetate and hexanes, recrystallization from 2-propanol gave off-white solid (0.5667 g, 33% yield). mp: 74-76° C. $^1$H NMR (CDCl$_3$): δ(ppm): 7.37 (m, 1H), 7.35 (t, 2H, J=7.5 Hz), 7.30-7.22 (m, 1H), 7.22 (m, 3H), 7.14 (d, 1H, J=9.5), 7.02 (td, 1H, J=8.3, 2.2 Hz), 5.89 (s, 1H), 3.08-2.87 (m, 4H).

2-(4-methylphenyl)-3-phenyl-2,3,5,6-tetrahydro-4H-1,3-thiazin-4-one: Recrystallization from 2-propanol gave white solid (1.2826 g, 75% yield). mp: 122-125° C. $^1$H NMR (CDCl$_3$): δ(ppm): 7.33-7.19 (m, 9H), 5.88 (s, 1H), 3.03-2.88 (m, 4H), 2.37 (s, 3H).

2-(3-methylphenyl)-3-phenyl-2,3,5,6-tetrahydro-4H-1,3-thiazin-4-one: After chromatography on 30 g silica gel with mixtures of ethyl acetate and hexanes, recrystallization from 2-propanol gave white solid (0.6438 g, 38% yield). mp: 110-110.5° C. $^1$H NMR (CDCl$_3$): δ(ppm): 7.34-7.13 (m, 9H), 5.87 (s, 1H), 3.08-2.87 (m, 4H), 2.38 (s, 3H).

2-(4-methoxyphenyl)-3-phenyl-2,3,5,6-tetrahydro-4H-1,3-thiazin-4-one: After chromatography on 30 g silica gel with mixtures of ethyl acetate and hexanes, recrystallization from ethyl acetate gave white solid (0.9103 g, 51% yield). mp: 157-160° C. $^1$H NMR (CDCl$_3$): δ(ppm): 7.32-7.20 (m, 7H), 6.90 (m, 2H), 5.89 Hz, 3.83 (s, 3H), 3.03-2.90 (m, 4H).

2-(3-methoxyphenyl)-3-phenyl-2,3,5,6-tetrahydro-4H-1,3-thiazin-4-one: Recrystallization from 2-propanol gave white solid (1.0193 g, 57% yield). mp: 127.5-128° C. $^1$H NMR (CDCl$_3$): δ(ppm): 7.36-7.29 (m, 3H), 7.25-7.22 (m, 3H), 7.01 (ddt, 1H, J=7.6, 1.8, 0.8 Hz), 6.95 (t, 1H, J=2.1 Hz), 6.86 (dd, 1H, J=8.1, 2.0 Hz), 5.87 (s, 1H), 3.83 (s, 3H), 3.11-2.87 (m, 4H).

3-(3-methoxyphenyl)-2-phenyl-2,3,5,6-tetrahydro-4H-1,3-thiazin-4-one: Chromatography on 30 g silica gel with mixtures of ethyl acetate and hexanes gave a yellow oil (1.4209 g, 79%). $^1$H NMR (CDCl$_3$): δ(ppm): 7.40 (m, 4H), 7.32 (m, 1H), 7.22 (t, 1H, J=8.1 Hz), 6.78 (m, 3H), 5.89 (s, 1H), 3.74 (s, 3H), 3.07-2.86 (m, 4H).

3-(3-nitrophenyl)-3-phenyl-2,3,5,6-tetrahydro-4H-1,3-thiazin-4-one: Recrystallization from 2-propanol gave yellow solid (0.893 g, 48%). mp: 133-135° C. $^1$H NMR (CDCl$_3$): δ(ppm): 8.08 (m, 2H), 7.54 (d, 1H, J=5.2 Hz), 7.47 (t, 1H, J=7.9 Hz), 7.39 (br. s, 4H), 7.34 (d, 1H, J=8.2 Hz), 5.97 (s, 1H), 3.01 (m, 4H).

3-(4-bromophenyl)-2-phenyl-2,3,5,6-tetrahydro-4H-1,3-thiazin-4-one: Recrystallization from 2-propanol gave an impure white solid (1.445 g, 69% yield). mp:104-105° C. $^1$H NMR (CDCl$_3$): δ(ppm): 7.43 (m, 2H), 7.38 (m, 3H), 7.33 (t, 1H, J=7.7 Hz), 7.09 (dd, 2H, J=8.8, 0.7 Hz), 5.86 (s, 1H), 2.97 (m, 4H).

3-(3-fluorophenyl)-2-phenyl-2,3,5,6-tetrahydro-4H-1,3-thiazin-4-one: After chromatography on 30 g silica gel with mixtures of ethyl acetate and hexanes, recrystallization from 2-propanol gave white solid (0.6538 g, 40% yield). mp: 79-81° C. $^1$H NMR (CDCl$_3$): δ(ppm): 7.40 (m, 4H), 7.33 (m, 1H), 7.28 (m, 1H), 6.97 (m, 3H), 5.90 (s, 1H), 2.96 (m, 4H).

3-(4-fluorophenyl)-3-phenyl-2,3,5,6-tetrahydro-4H-1,3-thiazin-4-one: After chromatography on 30 g silica gel with mixtures of ethyl acetate and hexanes, recrystallization from 2-propanol gave white solid (0.9607 g, 56% yield). mp: 102.5-103° C. $^1$H NMR (CDCl$_3$): δ(ppm): 7.39 (m, 4H), 7.33 (m, 1H), 7.17 (m, 2H), 7.00 (m, 2H), 5.86 (s, 1H), 3.01 (m, 3H), 2.90 (m, 1H).

2-phenyl-3-(3-(trifluoromethyl)phenyl)-2,3,5,6-tetrahydro-4H-1,3-thiazin-4-one: After chromatography on 30 g silica gel with mixtures of ethyl acetate and hexanes, an oil was obtained (0.9966 g, 49% yield). $^1$H NMR (CDCl$_3$): 7.48 (d, 2H, J=9.5 Hz), 7.43 (t, 1H, J=8.3 Hz), 7.39 (m, 5H), 7.34 (d, 1H, J=6.2 Hz), 5.93 (s, 1H), 2.99 (m, 4H).

2-(4-methylphenyl)-3-phenyl-2,3-dihydro-4H-pyrido[3,2-e][1,3]thiazin-4-one: Recrystallization of the crude material from 2-propanol gave orange-yellow solid (1.0572 g, 53% yield). mp: 128-130° C. $^1$H NMR (CDCl$_3$): δ(ppm): 8.51-8.47 (m, 2H), 7.47-7.29 (m, 7H), 7.24-7.21 (m, 1H), 7.10 (d, 2H, J=8.0 Hz), 6.15 (s, 1H), 2.29 (s, 3H).

3-(4-methylphenyl)-2-phenyl-2,3,5,6-tetrahydro-4H-1,3-thiazin-4-one: After chromatography on 30 g silica gel with mixtures of ethyl acetate and hexanes, an impure yellow solid was obtained (0.4603 g, 27% yield). mp: 81-85° C. $^1$H NMR (CDCl$_3$) (partial): δ(ppm): 5.78 (s, 1H).

2-(4-nitrophenyl)-3-phenyl-2,3-dihydro-4H-pyrido[3,2-e][1,3]thiazin-4-one: The crude solid was recrystallized from 2-propanol to give white crystals (1.3581 g, 62% yield). mp: 119-121° C. $^1$H NMR (CDCl$_3$): δ(ppm): 8.50 (m, 2H), 8.18 (d, 2H, J=8.8 Hz), 7.68 (d, 2H, J=8.8 Hz), 7.44 (m, 2H), 7.35 (m, 2H), 7.26 (dd, 2H, J=8.1, 4.8 Hz), 6.23 (s, 1H).

2-(3-bromophenyl)-3-phenyl-2,3-dihydro-4H-pyrido[3,2-e][1,3]thiazin-4-one: After chromatography on 30 g silica gel with mixtures of ethyl acetate and hexanes, recrystallization from 2-propanol gave light orange solid (0.7812 g, 33% yield). mp: 140-141° C. $^1$H NMR (CDCl$_3$): δ(ppm): 8.53 (dd, 1H, J=4.6, 1.7 Hz), 8.48 (dd, 1H, J=8.1, 1.8 Hz), 7.63 (s, 1H), 7.41 (m, 4H), 7.34 (m, 3H), 7.24 (dd, 1H, J=7.7, 4.8 Hz), 7.18 (t, 1H, J=7.9 Hz), 6.12 (s, 1H).

2-(4-bromophenyl)-3-phenyl-2,3-dihydro-4H-pyrido[3,2-e][1,3]thiazin-4-one: After chromatography on 30 g silica gel with mixtures of ethyl acetate and hexanes, recrystallization from 2-propanol gave orange solid (0.5016 g, 21% yield). mp: 176-178° C. $^1$H NMR (CDCl$_3$): δ(ppm): 8.52

(dd, 1H, J=4.6, 1.7 Hz), 8.46 (dd, 1H, J=7.9, 1.7 Hz), 7.43 (m, 4H), 7.34 (m, 5H), 7.23 (dd, 1H, J=8.1, 4.8 Hz), 6.12 (s, 1H).

2-(4-fluorophenyl)-3-phenyl-2,3-dihydro-4H-pyrido[3,2-e][1,3]thiazin-4-one: After chromatography on 30 g silica gel with mixtures of ethyl acetate and hexanes, recrystallization from toluene/hexanes gave off-white solid (0.5705 g, 28% yield). mp: 127.2-127.4° C. $^1$H NMR (CDCl$_3$): δ(ppm): 8.52 (dd, 1H, J=4.6, 1.7 Hz), 8.46 (m, 1H), 7.44 (m, 4H), 7.33 (m, 3H), 7.22 (m, 1H), 6.99 (t, 2H, J=8.4 Hz), 6.17 (s, 1H).

2-(3-(trifluoromethyl)phenyl)-3-phenyl-2,3-dihydro-4H-pyrido[3,2-e][1,3]thiazin-4-one: After chromatography on 30 g silica gel with mixtures of ethyl acetate and hexanes, recrystallization from toluene/hexanes gave off white solid (0.5764 g, 25% yield). mp: 114-119° C. $^1$H NMR (CDCl$_3$): δ(ppm): 8.52 (dd, 1H, J=4.7, 2.0 Hz), 8.48 (dd, 1H, J=7.9, 1.8 Hz), 7.73 (s, 1H), 7.66 (d, 1H, J=7.9 Hz), 7.55 (d, 1H, J=7.6 Hz), 7.43 (m, 3H), 7.33 (m, 3H), 7.24 (dd, 1H, J=7.9, 4.9 Hz), 6.21 (s, 1H).

2-(4-(trifluoromethyl)phenyl)-3-phenyl-2,3-dihydro-4H-pyrido[3,2-e][1,3]thiazin-4-one: After chromatography on 30 g silica gel with mixtures of ethyl acetate and hexanes, recrystallization from 2-propanol gave yellow solid (0.4330 g, 19% yield). mp: 169-172° C. $^1$H NMR (CDCl$_3$): δ(ppm): 8.52 (dd, 1H, J=4.8, 1.8 Hz), 8.48 (dd, 1H, J=7.7, 1.8 Hz), 7.43 (m, 2H), 7.34 (m, 3H), 7.24 (dd, 1H, J=8.4, 1.8 Hz), 6.20 (s, 1H).

2-(3-methylphenyl)-3-phenyl-2,3-dihydro-4H-pyrido[3,2-e][1,3]thiazin-4-one: After chromatography on 30 g silica gel with mixtures of ethyl acetate and hexanes, recrystallization from ethyl acetate/hexanes gave a light yellow solid (12% yield). mp: 112-113° C. $^1$H NMR (CDCl$_3$): δ(ppm): 8.50 (m, 1H), 8.47 (dd, 1H, J=7.7, 1.5 Hz), 7.41 (m, 2H), 7.35 (m, 2H), 7.31 (m, 1H), 7.26 (m, 2H), 7.20 (m, 2H), 7.08 (d, 1H, J=7.3 Hz), 6.13 (s, 1H), 2.31 (s, 3H).

2-(3-methoxyphenyl)-3-phenyl-2,3-dihydro-4H-pyrido[3,2-e][1,3]thiazin-4-one: After chromatography on 30 g silica gel with mixtures of ethyl acetate and hexanes, recrystallization from 2-propanol gave light orange crystals (0.3933 g, 19% yield). mp: 151-153° C. $^1$H NMR (CDCl$_3$): δ(ppm): 8.51 (dd, 1H, J=4.8, 1.5 Hz), 8.47 (dd, 1H, J=7.9, 1.3 Hz), 7.41 (m, 2H), 7.36 (m, 2H), 7.31 (m, 1H), 7.21 (m, 2H), 7.04 (d, 1H, J=7.0 Hz), 6.99 (s, 1H), 6.81 (dd, 1H, J=8.1, 2.2 Hz), 6.13 (s, 1H), 3.76 (s, 3H).

2-(4-methoxyphenyl)-3-phenyl-2,3-dihydro-4H-pyrido[3,2-e][1,3]thiazin-4-one: After chromatography on 30 g silica gel with mixtures of ethyl acetate and hexanes, recrystallization from 2-propanol gave yellow solid (1.1419 g, 53% yield). mp: 142.5-143° C. $^1$H NMR (CDCl$_3$): δ(ppm): 8.51 (dd, 1H, J=4.9, 1.8 Hz), 8.46 (dd, 1H, J=7.8, 2.0 Hz), 7.43-7.28 (m, 7H), 7.21 (dd, 1H, J=7.8, 4.7 Hz), 6.81 (m, 2H), 6.15 (s, 1H), 3.77 (s, 3H).

General Procedure for bis-(1,3-thiazin-4-ones): A two-necked 25-ml roundbottom flask was oven-dried, cooled under N$_2$, and charged with a stir bar, N,N'-(1,4-phenylene)bis(1-phenylmethanimine) (0.8531 g, 3 mmol) and 3-mercaptopropionic acid (0.6368 g, 6 mmol). 2-Methyltetrahydrofuran (2.3 ml) was added and the solution was stirred. Pyridine (1.95 ml, 24 mmol) and finally, 2,4,6-tripropyl-1,3,5,2,4,6-trioxatriphosphorinane-2,4,6-trioxide (T3P) in 2-methyltetrahydrofuran (50 weight %; 7.3 ml, 12 mmol) were added. The reaction was stirred at room temperature and followed by TLC (80% ethyl acetate/hexanes). The mixture was poured into a separatory funnel with dichloromethane and distilled water. The layers were separated and the aqueous layer was then extracted twice with dichloromethane. The organics were combined and washed with saturated sodium bicarbonate and then saturated sodium chloride. The organic was dried over sodium sulfate and concentrated under vacuum to give crude product. Further purification was carried out as indicated below for each compound.

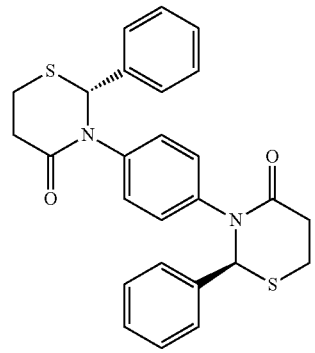 [SMILES: O=C1CCS[C@H](c2ccccc2)N1c1ccc(N2C(=O)CCS[C@H]2c2ccccc2)cc1]

meso-3,3'-(1,4-Phenylene)bis(2-phenyl-2,3,5,6-tetrahydro-4H-1,3-thiazin-4-one): The crude was recrystallized from CH$_2$Cl$_2$/acetone solution to give white powder (0.3108 g 1st crop, 0.0318 g 2nd crop, 25% total yield), m.p. 250° C. (decomp.). $^1$H NMR (CDCl$_3$): δ(ppm): 7.39-7.31 (m, 10H), 7.17 (d, 4H, J=5.2 Hz), 5.85 (s, 2H), 3.00-2.91 (m, 8H).

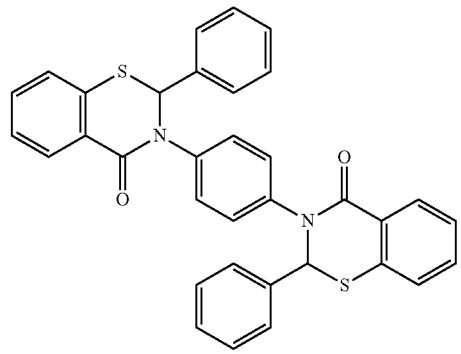 [SMILES: O=C1c2ccccc2SC(c2ccccc2)N1c1ccc(N2C(=O)c3ccccc3SC2c2ccccc2)cc1]

3,3'-(1,4-Phenylene)bis(2-phenyl-5,6-dihydro-4H-1,3-benzothiazin-4-one): The crude was recrystallized from CH$_2$Cl$_2$/acetone solution to give white powder (0.1894 g, 11% yield), m.p. 307° C. (decomp.). $^1$H NMR (CDCl$_3$): δ(ppm): 8.21 (d, J=7.8 Hz, 2H), 7.41 (d, J=7.7 Hz, 4H), 7.35-7.33 (m, 4H), 7.30-7.24 (m, 10H), 7.17 (d, J=7.8 Hz, 2H), 6.04 (s, 2H)

Although the present invention has been described in terms of specific exemplary embodiments and examples, it will be appreciated that the embodiments disclosed herein are for illustrative purposes only and various modifications and alterations might be made by those skilled in the art without departing from the spirit and scope of the invention as set forth in the following claims.

REFERENCES

All references cited herein including those below are hereby incorporated by reference in their entirety.
1. Qu, H.; Zhang, R.; Hu, Y.; Ke. Y.; Gao, Z.; Xu, H. Z. Naturforsch., C: J. Biosciences 2013, 68, 77-81.

2. Dandia, A.; Singh, R.; Arya, K. *Phosphorus, Sulfur and Silicon and the Related Elements* 2004, 179, 551-564.
3. Krumkains, E. V. EP 10420 B1 (1984).
4. Chen. Y.; Wu, J.; Yu. L.; Zhai, D.; Yi, Z.; Luo, J.; Liu, M. CN102653526 A (2012).
5. Arya, K.; Rawat, D. S.; Dandia, A.; Sasai, H. *J. Fluor. Chem.* 2012, 137, 117-122.
6. Dandia, A.; Singh, R., Saini, D. *J. Chem. Sci.* 2013, 125, 1045-1053.
7. Choi, H.; Wang, Z.; Zhu, X.; He, X.; Yang, K.; Liu, H. WO 2008112674 A1 (2008).
8. Chen. Y.; Wu, J.; Yu. L.; Zhai, D.; Yi, Z.; Luo, J.; Liu, M. CN102653526 A (2012).
9. Mei, Z.; Wang, L.; Lu, W.; Pang, C.; Maeda, T.; Peng, W.; Kaiser, M.; El Sayed, I.; Inokuchi, T. *J. Med Chem.* 2013, 56, 1431-1442.
10. Li, Q.; Li, C; Lu, X.; Zhang, H.; Zhu, H. *Eur. J. Med. Chem.* 2012, 50, 288-295.
11. Wang, S.; Fang, K.; Dong. G.; Chen, S.; Liu, N.; Miao, Z.; Yao, J.; Li, J.; Zhang, W.; Sheng, C. *J. Med. Chem.* 2015, 58, 6678-6696.
12. Kamel, M. M.; Ali, H. I.; Anwar, M. M.; Mohamed, N. A.; Soliman, A. M. M. *Eur. J. Med. Chem.* 2010, 45, 572.
13. Popiolek, L.; Biernasiuk, A.; Malm, A. *J. Heterocycl. Chem.* 2016, 53, 479-486.
14. Jeng, F.; Li, X.; Shao, J.; Zhu, M.; Li, Y.; Hua, C.; Xiaoliu, L. *Chin. J. Org. Chem.* 2015, 35, 1370-1374.
15. Hou, Y.; Xing, S.; Shao, J.; Yin, Z.; Hao, L.; Yang, T.; Zhang, H.; Zhu. M., Chen, H.; Li, X. *Carbohydr. Res.* 2016, 429, 105-112, and references cited therein.
16. Nofal, Z. M.; Soliman, E. A.; El-Karim, A.; El-Zahar, M. I; Srour, A. M.; Sethumadhavan, S.; Maher, T. J. *J. Heterocycl. Chem.* 2014, 51, 1797-1806.
17. Mandour, A. H.; El-Sawy, E. R.; Ebid, M. S.; El-Sayed, Z. G. *Egypt. J. Chem.* 2007, 50, 555-568.
18. Zarghi, A.; Zebardast, T.; Daraie, B.; Hedayati, M. *Bioorg. Med. Chem.* 2009, 17, 5369-5373.
19. Welsch, M. E.; Snyder, S. A.; Stockwell, B. R. *Curr. Opin. Chem. Biol.* 2010, 14, 347-361.
20. Arya, K.; Tomar, P.; Singh, J. *RSC Adv.* 2014, 4, 3060-3064.
21. Shreedhara, S. H.; Vagdevi, H. M.; Jayanna, N. D.; Raghavendra, R. *Internat. J. Pharma Res. Health Sci.* 2017, 56, 2055-2063.
22. Li, X.; Qin, Z.; Yang, T.; Zhang, H.; Wei, S.; Li, C.; Chen, H.; Meng, M. *Bioorg. Med. Chem. Lett.* 2012, 22, 2712-2716.
23. Yennawar, H. P.; Singh, H.; Silverberg, L. *J. Acta Cryst., Sect. E: Struct. Rep. Online* 2014, E70, o638.
24. Yennawar, H. P.; Bendinsky, R. V.; Coyle, D. J.; Cali, A. S.; Silverberg, L. *J. Acta Cryst., Sect. E: Struct. Rep. Online* 2014, E70, o465.
25. Yennawar, H. P.; Silverberg, L. *J. Acta Cryst.*, Sect. E: Struct. Rep. Online 2014, E70, o133. Corrigendum. 2015, E71, e5.
26. Yennawar, H. P.; Singh, H.; Silverberg, L. *J. Acta Cryst., Sect. E: Crystallogr. Commun.* 2015, E71, 62-64.
27. Yennawar, H. P.; Cali, A. S.; Xie, Y.; Silverberg, L. *J. Acta Cryst., Sect. E: Crystallogr. Commun.* 2015, E71, 414-417.
28. Silverberg, L. J.; Pacheco, C. N.; Lagalante, A.; Cannon, K. C.; Bachert, J. T.; Xie, Y.; Baker, L.; Bayliff, J. A. *Int. J. Chem.* (Toronto, ON, Can.) 2015, 7 (2), 150-162.
29. Yennawar, H. P.; Coyle, D. J.; Noble, D. J.; Yang, Z.; Silverberg, L. *J. Acta Cryst., Sect. E: Crystallogr. Commun.* 2016, E72, 1108-1112.
30. Silverberg, L. J.; Tierney, J.; Pacheco, C.; Lagalante, A.; Bachert, J. T.; Bayliff, J. A.; Bendinsky, R. V.; Cali, A. S.; Chen, L.; Cooper, A. D.; Minehan, M. J.; Mroz, C. R.; Noble, D. J.; Weisbeck, A. K.; Xie, Y.; Yang, Z. *Arkivoc* 2016, (vi), 122-143.
31. Yennawar, H. P.; Buchwalter, M. J.; Colburn, B. K.; Silverberg, L. *J. Acta Cryst., Sect. E: Crystallogr. Commun.* 2018, E74, 363-366.
32. Yennawar, H. P.; Bradley, H. G.; Perhonitch, K. C.; Reppert, H. E.; Silverberg, L. *J. Acta Cryst., Sect. E: Crystallogr. Commun.* 2018, E74, 454-457.
33. Yennawar, H. P.; Moyer, Q. J.; Silverberg, L. *J. Acta Cryst., Sect. E: Crystallogr. Commun.* 2018, E74, 1497-1499.

We claim:

1. A compound of Formula I:

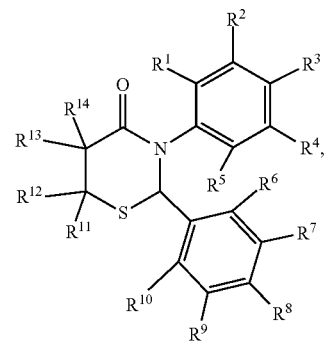

wherein $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ are each independently selected from the group consisting of H, halogen, nitro, cyano, amido, pyridyl, alkyl, aryl, acyl, alkoxy, cycloalkyl, heteroalkyl, heterocyclyl, aralkyl, heteroaryl and heteroaralkyl, wherein $R^8$ is not H or $CH_3$, and wherein $R^3$ is not H, $CH_3$ or an aza-aromatic group.

2. The compound of claim 1, wherein $R^1$, $R^2$, $R^4$, $R^5$, $R^6$, $R^7$, $R^9$, $R^{10}$ $R^{11}$, $R^{12}$, $R^{13}$ and $R^{14}$ are each independently selected from the group consisting of H, halogen, nitro, amido, alkyl, alkoxy and acyl.

3. The compound of claim 1, wherein $R^3$ is a thiazinone.

4. A compound of Formula II

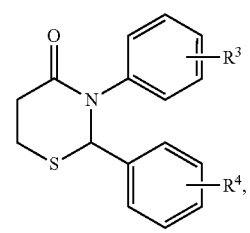

wherein $R^3$ is H; and $R^4$ is selected from the group that consists of m-Br, p-Br, m-F, p-F, m-$CF_3$, p-$CF_3$, m-$OCH_3$ and p-$OCH_3$.

5. A compound of Formula II

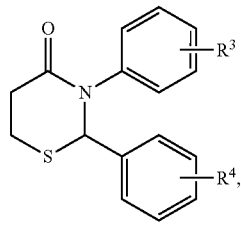

II wherein R³ is selected from a group consisting of m-NO₂, m-Br, p-Br, m-F, p-F, m-CF₃, p-CF₃, m-OCH₃, p-OCH₃ and p-thiazinone; and
wherein R⁴ is H.

6. The compound of claim 5, wherein R³ is selected from the group consisting of m-NO₂, p-Br, m-F, p-F, m-CF₃, and m-OCH₃.

7. A compound of Formula III

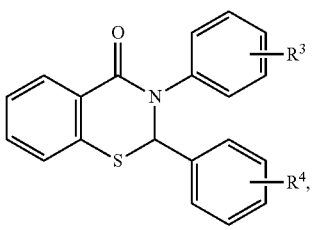

III wherein R³ and R⁴ are each selected from the group that consists of m-Br, p-Br, m-F, p-F, m-CF₃, p-CF₃, m-OCH₃ and p-OCH₃; and R³ is the same as R⁴.

8. The compound of claim 7, wherein R³ and R⁴ are each selected from the group consisting of m-Br, p-Br, m-F, p-F, p-CF₃, m-OCH₃ and p-OCH₃.

9. A compound of Formula IV

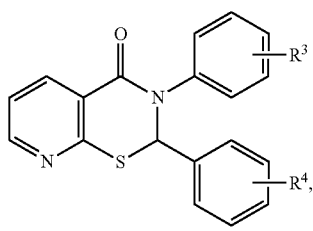

IV wherein R³ is H, and
wherein R⁴ is selected from the group consisting of m-NO₂, m-Br, p-Br, m-CF₃, p-CF₃, m-OCH₃ and p-OCH₃.

* * * * *